United States Patent
Herr et al.

(12)

(10) Patent No.: US 6,258,364 B1
(45) Date of Patent: *Jul. 10, 2001

(54) PURIFIED SPERM SURFACE ANTIGEN, MONOCLONAL ANTIBODY THEREFOR AND APPLICATION THEREFOR

(75) Inventors: John C. Herr; Alan B. Diekman; V. Anne Westbrook-Case; Elizabeth J. Norton, all of Charlottesville, VA (US)

(73) Assignee: University of Virginia Patent Foundation, Charlottesville, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/027,673

(22) Filed: Feb. 23, 1998

Related U.S. Application Data (63) Continuation-in-part of application No. 08/671,622, filed on Jun. 28, 1996, now Pat. No. 5,830,472.

(51) Int. Cl.$^7$ .................................................. A61K 45/00
(52) U.S. Cl. ................. 424/279.1; 530/395; 536/1.11
(58) Field of Search .................................... 530/395, 350; 424/279.1, 184.1; 536/1.11

(56) References Cited

FOREIGN PATENT DOCUMENTS

WO 90/09802    9/1990 (WO) .

OTHER PUBLICATIONS

Matsudaira, Methods in Enzymology, vol. 182, 1992 pp. 602–605.*

K. Kameda, et al., Biology of Reproduction, vol. 46, pp. 349–357, "Comparative Studies of the Antigens Recognized by Sperm–Immobilizing Monoclonal Antibodies", 1992.

* cited by examiner

Primary Examiner—Patrick J. Nolan
(74) Attorney, Agent, or Firm—John P. Breen (57) ABSTRACT

S19 mAb, deposited under Accession Number HB-12144 at the ATCC, binds to a carbohydrate epitope of a glycoprotein found distributed over the surface of sperm. The carbohydrate nature of the epitope, its distribution over the entire sperm surface, and the fact that it is epididymal/sperm specific and not naturally found in any of the tissues of the female reproductive tract, make the glycoprotein, SAGA-1, a desirable immunogen as the active agent for a contraceptive vaccine, as well as a test standard for monitoring antibody titer. The antibody provides a diagnostic for the presence of sperm, as well as a topical spermistatic.

2 Claims, 7 Drawing Sheets

SAGA-1    G  Q  N  D  T  S  Q  X(S) (S) (P)
          |  |  |  |  |  |  |   |   |   |
CDW52     G  Q  N  D  T  S  Q  T S   S   P

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence:N-terminal
      amino acid sequence
<220> FEATURE:
<221> NAME/KEY: UNSURE
<222> LOCATION: (8)

<400> SEQUENCE: 1

Gly Gln Asn Asp Thr Ser Gln Xaa Ser Ser Pro
  1               5                  10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence:N-terminal
      amino acid sequence

<400> SEQUENCE: 2

Gly Gln Asn Asp Thr Ser Gln Thr Ser Ser Pro
  1               5                  10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:N-terminal
      amino acid sequence

<400> SEQUENCE: 3

Gly Gln Asn Asp Thr Ser Gln
  1               5
```

PURIFIED SPERM SURFACE ANTIGEN, MONOCLONAL ANTIBODY THEREFOR AND APPLICATION THEREFOR

This application is a Continuation-in-part application of U.S. patent application 08/671,622, filed Jun. 28, 1996, U.S. Pat. No. 5,830,472. The entire disclosure of this earlier-filed patent application is incorporated herein by reference.

US GOVERNMENT RIGHTS

This invention was made with United States Government support under Grant Nos. T32 HD07382, T32 DK07642 and U54 HD29099 awarded by the National Institutes of Health. The United States Government has certain rights in the invention.

FIELD OF THE INVENTION

This invention pertains to the characterization and development of the tissue specific, sperm surface glycoprotein SAGA-1, as well as methods of use of the same. This potential immunogen, recognized and bound by the S19 antibody, was first disclosed in Parent Application U.S. application Ser. No. 671,622 filed Jun. 28, 1996. Herein, the epitope recognized by the S19 antibody is demonstrated to be a carbohydrate epitope, the immunogen a component of the matrix which constitutes the coat or surface of human spermatozoa, and the glycoprotein shown to be produced by the epididymis. These features demonstrate the utility of the SAGA-1 glycoprotein, and/or the carbohydrate epitope thereof, as contraceptive immunogens, effective in the preparation of a contraceptive vaccine. Similarly, the utility of the S19 monoclonal antibody as an effective spermicide or "spermistatic" (sperm-binding agent and penetration inhibitor) are reinforced, demonstrating the utility of an antibody which binds this unique epitope as a topical contraceptive. Similarly, the titer of antibodies to SAGA-1 can be used as an indicator of the potential fertility of individuals being treated with the contraceptive vaccine. Further, the S19 monoclonal antibody can be used as the active agent in an immunodiagnostic kit and assay to detect the presence of sperm in a biological sample, such as ejaculate or post coital vaginal lavage.

BACKGROUND OF RELATED WORK

Previously described contraceptive vaccine candidates represent recombinant protein or synthetic peptide immunogens. However, the S19 carbohydrate epitope and other SAGA-1-specific carbohydrate epitopes are components of the sperm glycocalyx, the extracellular matrix of carbohydrate that coats the surface of human spermatozoa. Carbohydrate immunogens provide opportunity for improved immunocontraceptive effects over peptide immunogens as carbohydrate epitopes are more accessible to antibody binding. This is due to the generally protruding character of the carbohydrate chain of a glycoprotein into an aqueous environment, as opposed to short chain peptides or conformational epitopes, which may be obscured or lost depending on the binding conditions.

As more fully described in the parent application, the improvement of available contraceptive methods receives substantially continuous attention. Currently available spermicides employ detergents, specifically, varieties of Nonoxynol-9. The use of this detergent spermicide has been implicated in increasing frequency of urogenital, cervical, and vaginal inflamation in women employing the same. As an alternative, the use of antibodies as "spermicides" has been suggested. See generally Alexander, Scientific American, September: 136–141 (1995).

One antibody studied in terms of its sperm-binding potential is the S19 monoclonal antibody. This monoclonal antibody is described, but not enablingly disclosed, in Anderson et al., J. Reprod. Immunol., 10:1031–257 (1987). This antibody strongly agglutinates human sperm, inhibits tight binding between human sperm and the zona pellucida and blocks sperm penetration of cervical mucus. Mahoney et al., J. Reprod. Immunol., 19:269–285.

The monoclonal antibody of S19 is expressed by the hybridoma cell line deposited at the ATTC, in 10801 University Blvd., Manassas, Va. 20110-2209, USA on Jun. 26, 1996, under accession number HB-12144. This deposit was made pursuant to the Budapest Treaty, and all restrictions thereon will be irrevocably removed upon issuance of a patent on the pending parent application, which has been allowed. Notwithstanding the early publication identifying the existence of the antibody, the same was not made available, or otherwise publicly used or sold, until after the filing of the parent application in June of 1996. The experiments described in Mahoney et al., Supra, were conducted under the control of inventor John Herr, and thus, the S19 monoclonal antibody is the subject of the claims of the parent patent to issue.

While work has continued on topical contraceptives, interest continues in developing a contraceptive vaccine, based on the use of sperm antigens. Decreased fertility rates have been obtained through the immunization of test animals with sperm surface antigens such as LDH-C4, O'Hern et al., Biol. Reprod. 52:331–339 (1995), PH-20, Primakoff et al., Nature 335:543–546 (1988), RSA-1, O'Rand et al., J. Reprod. Immunol. 25:89–102 (1993) and fertilin, Ramarao et al., Mol. Reprod. Dev., 43:70–75 (1995). Unfortunately, as observed in the parent case, the highest rate of efficacy observed in vaccines of this type is about 75% inhibition of fertility. While impressive as an experimental development, this is far below the threshold necessary to provide an acceptable and safe contraceptive vaccine at a level comparable to oral contraceptives and other methods commercially available.

SUMMARY OF THE INVENTION

SAGA-1 was identified with a murine monoclonal antibody (mAb), S19, that agglutinates human spermatozoa, inhibits sperm-zona binding, blocks sperm penetration of cervical mucus, and induces the shaking phenomenon. SAGA-1 is also recognized by H6-3C4, a human sperm-agglutinating mAb produced using lymphocytes from an immunologically infertile woman. The human H6-3C4 antibody and the function-inhibitory mAb S19 recognize carbohydrate epitopes present on the SAGA-1 glycoprotein. Microsequence analysis demonstrated that SAGA-1 is related to CDw52, a GPI-anchored protein first identified on lymphocytes and involved in signal transduction. Cdw52 is bound by CAMPATH-1M mAb. The S19 and H6-3C4 carbohydrate epitopes are not present on the CDw52 glycoprotein. Therefore, SAGA-1 and CDw52 represent glycoforms, i.e. glycoprotein isoforms that have the same peptide sequence but possess different oligosaccharide side chains. SAGA-1 is important, therefore, due to its involvement in gamete interactions during fertilization, the fact that it is a glycoprotein on the entire sperm surface, and it serves as a target for isoantibodies involved in the female immune response to spermatozoa. For these reasons, SAGA-1 is a superior immunogen as an active agent in an immunocontraceptive vaccine.

BRIEF DESCRIPTION OF THE DRAWINGS

FIGS. 1–10 are electrophotographic reproductions of photographs of varies aspects of the analysis of SAGA-1 and its characteristics.

FIG. 1 reflects agglutination of spermatozoa with the SAGA-1 binding antibody S19.

FIG. 2 is a Western blot analysis of sperm extracts electrophoresed on a polyacrylamide-SDS gel, then reacted with S19 antibody. Binding is shown in FIG. 2A.

FIG. 3 reflects a Western blot analysis of two-dimensional electrophoresed SAGA-1 protein. FIG. 3A shows staining with Protogold, while

FIG. 4 reflects analysis of sperm extract phase partitioned with Triton X-114, with FIG. 4A reflecting amido black staining, FIG. 4B immunoblotting with S19 and FIG. C immunoblotting with MHS-10. In each figure, lane 1 reflects whole sperm extract, lane 2 the detergent phase, and lane 3 the aqueous phase.

FIG. 5 reflects two-dimensional immunoblotting of PI-PLC reaction supernatants with S19.

FIG. 8 reflects two-dimensional immunoblots of sperm proteins, FIG. 8A reflects immunoblotting with S19, FIG. 8B reflecting immunoblotting with CAMPATH-1M monoclonal antibody.

FIG. 9A shows binding with sperm extracts and FIG. 9B shows binding with spleen extracts.

FIG. 10 shows immunohistochemical analysis of human epididymis using differential interference microscopy.

DETAILED DESCRIPTION OF THE INVENTION

The characterization and further development of SAGA-1 as a contraceptive immunogen has shown its superior characteristics through multiple steps. Similarly, further characterization of the binding properties of the S19 mAb has demonstrated its effective agglutination of sperm, and reinforced its suitability as both a topical contraceptive agent, and a reagent to confirm the presence of sperm in an ejaculate, or a sample derived from an ejaculate, such as a fluid sample drawn from a female reproductive tract following coitus. In this application, a topical contraceptive that acts to agglutinate and/or bind sperm and thereby prevent sperm passage is referred to as a "spermistatic" to distinguish it from conventional detergent-based spermicides.

The invention is disclosed below by reference to steps undertaken to characterize the antibody and immunogen, followed by a discussion in detail of the utilities offered by these agents.

Properties of the S19 mAb

The Anti-SAGA-1 S19 mAb Agglutinates all Spermatozoa in Human Semen in a "Tangled" Pattern of Agglutination.

Figure 1A:
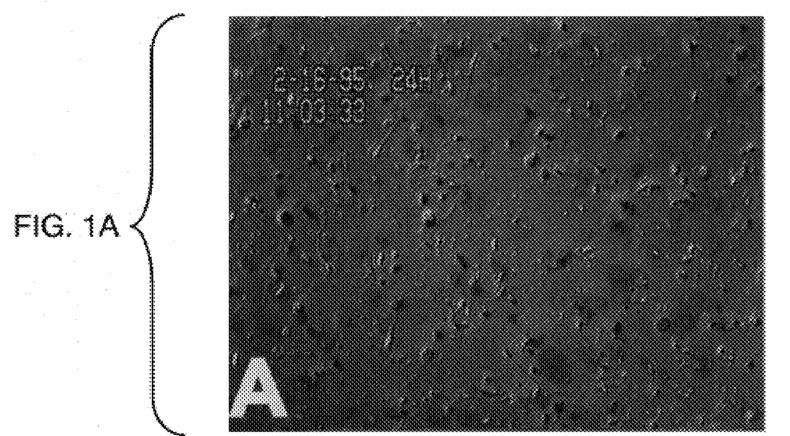
FIG. 1A reflects a mixture of sperm and S19 ascites fluid immediately after combination, showing free-swimming spermatozoa.
Figure 1B:
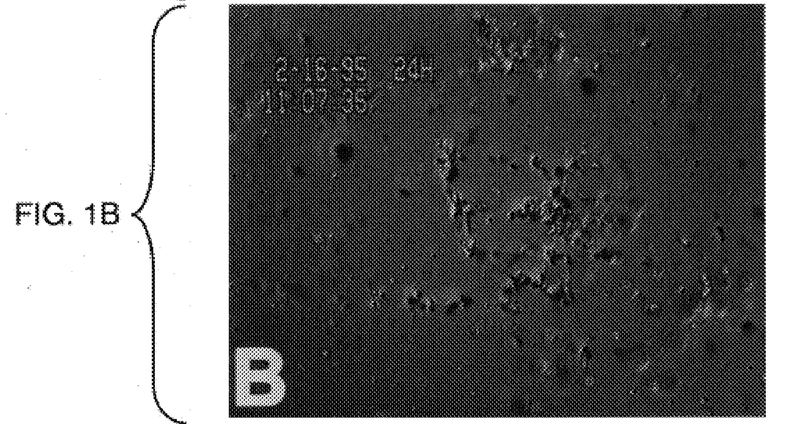
FIG. 1B is a photograph of the same mixture after four minutes reflecting the initial formation of agglutination floccules.
Figure 1C:
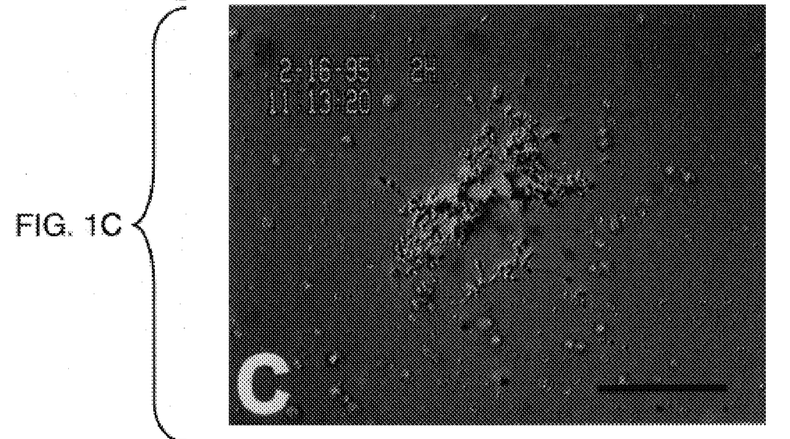
FIG. 1C reflects the same mixture after ten minutes, showing thorough agglutination of human sperm.

The agglutination of human spermatozoa by the S19 mAb was videotaped to obtain a continuous record of the process. For each experiment, human semen was diluted to a final concentration of 20 million spermatozoa/ml and ascites was diluted 1:10. Sperm and ascites were mixed in an Eppendorf tube and then placed on a hemacytometer. Immediately following the mixture of diluted semen and ascites (Time=0), free-swimming spermatozoa were evenly distributed across the field of view (FIG. 1A). Viable spermatozoa, non-motile spermatozoa, round cells, and debris were evident. After 4 minutes, agglutination floccules had begun to form and the number of free-swimming spermatozoa was decreased (FIG. 1B). After 10 minutes, spermatozoa were tightly bound in agglutination floccules in the "tangled" pattern described by Rose et al. Clin. Exp. Immunol. 23:175–179 (1976); head-to-head, tail-to-tail, and head-to-tail binding was evident (FIG. 1C). After 30 minutes, all spermatozoa were agglutinated and no free-swimming spermatozoa were evident. Control null ascites demonstrated no sperm-agglutinating activity throughout the time course. (FIG. 1: Agglutination of human spermatozoa with the S19 mAb. Scale bar=100 $\mu$m.)

The Anti-SAGA-1 S19 mAb Inhibits Sperm Penetration of Cervical Mucus and Induces the Shaking Phenomenon.

The ability of the S19 mAb to inhibit the penetration of bovine cervical mucus was examined using the TruTrax assay (Humagen, Charlottesville, Va.) following the manufacturer's instructions with modification. Mouse ascites containing the S19 mAb was mixed with bovine cervical mucus reconstituted from lyophilized powder. The S19-cervical mucus mixture was injected into the TruTrax capillary chamber. An aliquot of human semen was placed at the end of the capillary chamber, spermatozoa were allowed to penetrate the cervical mucus, and their progress was observed by light microscopy. In regions of high sperm density, spermatozoa were agglutinated in the "tangled" pattern observed with the slide agglutination assay described above. In regions where agglutination could not occur due to low sperm concentration, individual spermatozoa were immobilized and exhibited the quivering effects of the shaking phenomenon Kremer and Jager Fertil. Steril. 27:335–340 (1976). These effects were not observed with control null ascites. These results are significant since induction of the shaking phenomenon by antibody binding to a specific sperm surface antigen has not been reported. Furthermore, the S19 mAb provides a valuable reagent for elucidation of this potential mechanism of immunologic infertility.

The S19 mAb Recognizes a Carbohydrate Epitope on the SAGA-1 Glycoprotein.

Figure 2A:
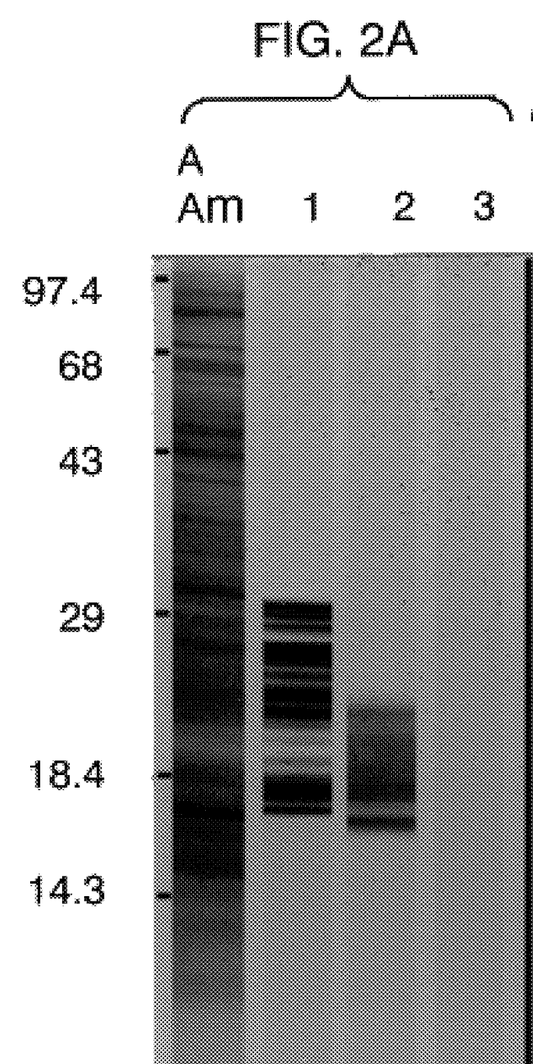
Figure 2B:
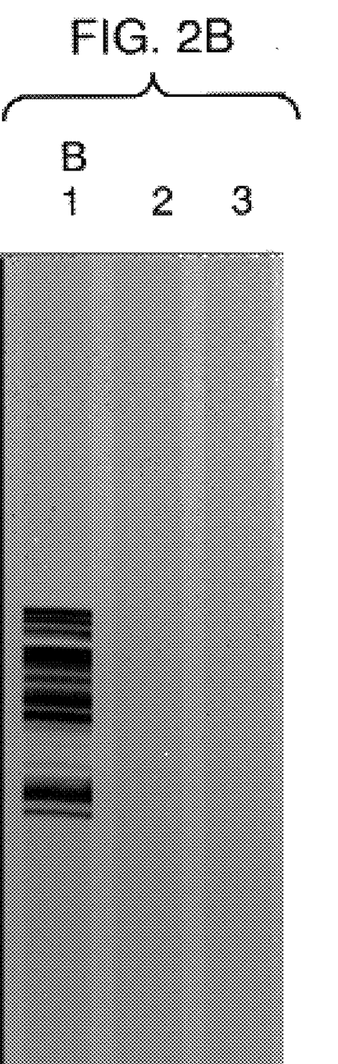
In FIG. 2B, the same experiment was performed after treatment of the extract with 10 mM periodic acid. S19 mAb did not bind indicating a carbohydrate epitope, sensitive to periodic acid. In the same figures, binding with the antibody MHS-10, which binds the SP-10 protein is shown in lane 1, with a control shown in lane 3.

The molecular characteristics of SAGA-1 were studied by Western blot analysis of sperm extracts following varied chemical, enzymatic, and electrophoretic treatment. On immunoblots of a 1% SDS human sperm extract electrophoresed on a one-dimensional, 15% polyacrylamide-SDS gel, the S19 mAb reacted with a series of overlapping bands that ranged from approximately 15 to 25 kDa (FIG. 2A, lane 2). S19 reactivity with the cognate antigen was abolished by treatment with 10 mM periodic acid (FIG. 2B, lane 2) while the reactivity of the MHS-10 mAb with a peptide epitope of the SP-10 protein was unaffected (FIG. 2A and B, lane 1). MHS-10 mAb and SP-10 immunogen are fully disclosed and characterized in U.S. Pat. No. 5,436,137 which is incorporated herein by reference. This finding indicated that the epitope recognized by the S19 mAb is a carbohydrate moiety. Treatment with proteinase K destroyed protein material in a sperm extract; this proteolysis also removed S19 immunoreactivity, indicating that the S19 carbohydrate epitope was associated with a protein present in the extract. These findings suggest that the S19 mAb immunoreacted with a carbohydrate epitope of the SAGA-1 glycoprotein. (FIG. 2: A, Immunoblot incubated with mAbs; B, Immunoblot incubated with mAbs following treatment with 10mM periodic acid. Am, amido black staining; lane 1, MHS-10; lane 2, S19; lane 3, null ascites.)

The immunoreactivity of the S19 mAb with sperm extracts from eight different donors was very similar. The same series of SAGA-1 glycoprotein bands was present in each sperm extract, although the relative intensity of immunoreactivity with specific bands varied among individuals. To date, the S19 mAb has not failed to react with any sperm sample tested (n>50) by Western blot, agglutination assay, and/or immunofluorescence, indicating the S19 epitope is well conserved in the human population.

Characterization of the SAGA-1 Immunogen
SAGA-1 is a Highly Acidic Glycoprotein.

Figure 3A:
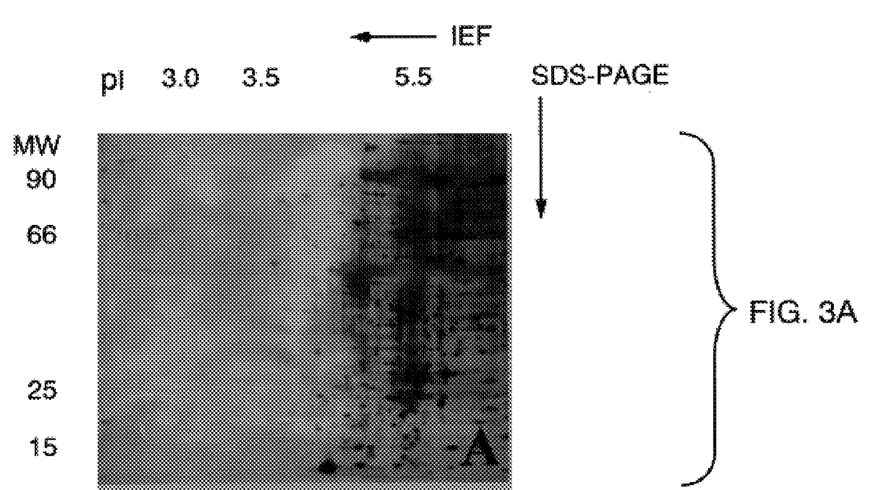
Figure 3B:
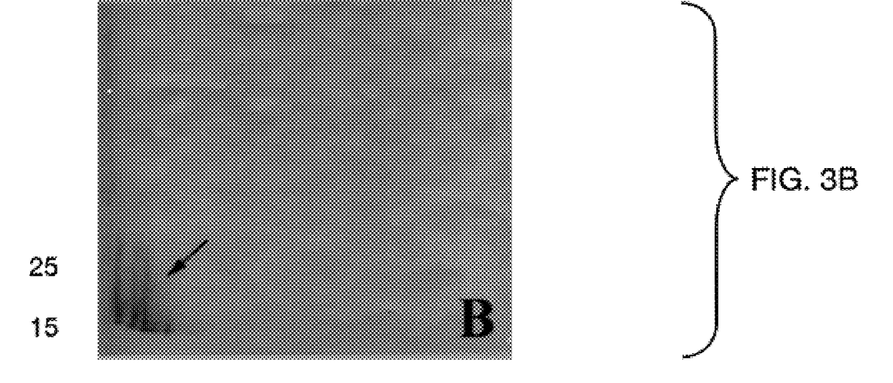
FIG. 3B shows S19 immunoreaction with the isoforms of SAGA-1.

Sperm proteins extracted in 2% octyl glucoside were separated by two-dimensional gel electrophoresis. The first dimension isoelectric focusing gel was formulated to separate protein over an acidic pH range. The separated proteins were analyzed by Western blotting. The S19 mAb immunoreacted with a series of spots that ranged in apparent molecular weight from 15 to 25 kDa and that ranged in isoelectric point (pI) from approximately 2.5 to 3.0 (FIG. 3B). These immunoreactive protein spots did not stain with Protogold possibly due to the negative charge of SAGA-1 (FIG. 3A). Furthermore, the apparent pI of SAGA-1 increased to 4.0 to 4.5 following treatment with neuraminidase, indicating that the SAGA-1 carbohydrate structure is partially composed of sialic acid. (FIG. 3: Two-dimensional electrophoresis and Western blot analysis of SAGA-1.)

SAGA-1 is a Hydrophobic, Membrane Protein.

SAGA-1 was not detected in human sperm extracts prepared with high salt (1 M NaCl or 0.6 M KCL) and/or mild non-ionic detergent (0.1% NP-40 or Triton X-100). These results indicated that SAGA-1 is not extracted with treatments classically used to remove peripheral proteins van Renswoude and Kempt, Meth. Enzymol. 104:329–339 (1984).

Further evidence that SAGA-1 exists as a membrane protein was examined using Triton X-114 phase partitioning as described by Bordier, J. Biol. Chem., 256:1604–1607 (1981). Non-ionic detergents, such as Triton X-114, solubilized integral membrane proteins by replacing the normal lipid environment. Triton X-114 forms small micelles at 0° C. when dispersed in aqueous solution above its critical micelle concentration. Hydrophobic membrane proteins are incorporated into these micelles while hydrophillic proteins remain in the aqueous environment. When such a solution is heated, the micelles increase in size and come out of solution forming a detergent-rich phase that can be separated from the aqueous solution by centrifugation. Bordier, Supra used this method to demonstrate that most integral membrane proteins and GPI-anchored proteins partition with the detergent phase while hydrophilic proteins remain in the aqueous phase.

Figure 4A:
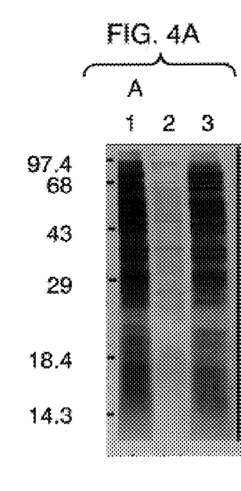
Figure 4B:
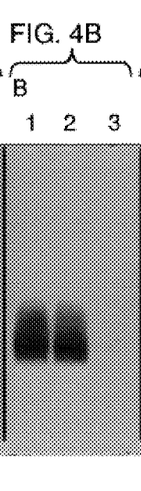
Figure 4C:
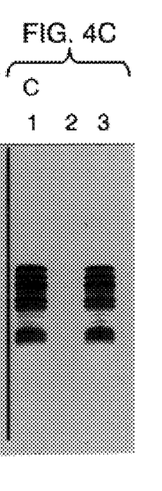

To study Triton X-114 phase partitioning of SAGA-1, washed human spermatozoa were extracted in 1% Triton X-114, 10 mM Tris-HCl, pH 7.4, 150 mM NaCl at 4° C. and centrifuged to remove debris. Following three cycles of phase partitioning, equivalent amounts of the initial sperm extract, the detergent phase, and the aqueous phase were analyzed by SDS-PAGE and immunoblotting (FIG. 4). The human sperm/testis-specific protein SP-10, a peripheral, acrosomal membrane protein served as a control; reactivity of the MHS-10 mAb with SP-10 was detected in the aqueous phase (FIG. 4C). S19 reactivity was detected in the initial sperm extract and in the detergent phase but not in the aqueous phase (FIG. 4B). These results indicate that the S19 mAb reacts with a hydrophobic, membrane glycoprotein that may be either an integral membrane protein or GPI-anchored protein. Amido black staining showed that the majority of total sperm protein remained soluble in the aqueous phase while few proteins partitioned with Triton X-114 (FIG. 4A). Therefore, Triton X-114 phase partitioning is a useful step in the purification of native SAGA-1. (FIG. 4: A, Amido black staining; B, Immunoblot with S19; C, Immunoblot with MHS-10. Lane 1, whole Triton X-114 sperm extract; Lane 2, detergent phase; Lane 3, aqueous phase.)

Similar hydrophobic properties were identified following extraction of human spermatozoa with chloroform/methanol/water (3:8:4). Immunoblot analysis with the S19 mAb detected SAGA-1 in the fraction of proteins that were soluble in chloroform/methanol providing another enrichment method to purify this glycoprotein.

SAGA-1 is a GPI-Anchored Glycoprotein.

Figure 5A:
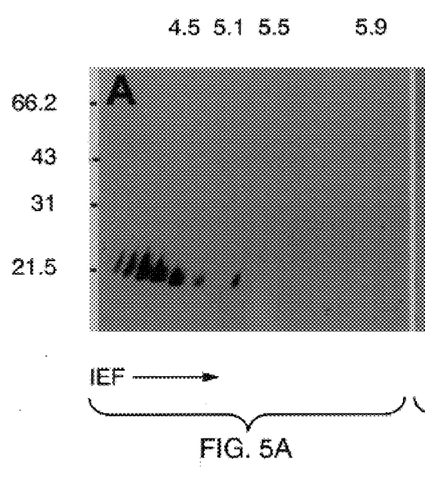
FIG. 5A is the supernatant containing protein liberated by PI-PLC cleavage, while FIG. 5B reflects the "minus" control reaction.
Figure 5B:
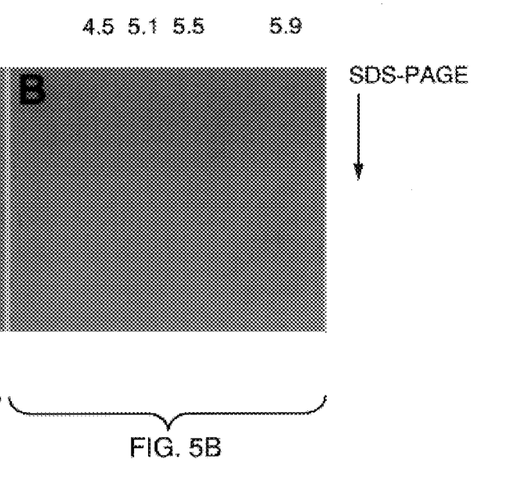

Intact human spermatozoa were isolated over a discontinuous Percoll gradient (55%–80%) and incubated in suspension with B. thuringiensis phosphatidylinositol-specific phospholipase C (PI-PLC) which cleaves GPI-anchor structures Ferguson (1993). The supernatants were examined by two-dimensional immunoblot analysis with the S19 mAb for the presence of the SAGA-1 glycoprotein (FIG. 5). SAGA-1 was identified in the PI-PLC reaction supernatant that contained proteins liberated from the sperm surface by enzyme cleavage. S19 immunoreactivity was absent in control supernatants from minus-PI-PLC and heat-inactivated PI-PLC reactions. These results indicate that SAGA-1 is anchored in the sperm plasmalemma via a GPI-lipid linkage. (FIG. 5: Two dimensional immunoblot analysis of PI-PLC reaction supernatants with the S19 mAb. A, Supernatant containing protein liberated by PI-PLC cleavage; B, Supernatant from minus-PI-PLC control reaction.)

SAGA-1 was Identified with the S19, H6-3C4, and Related mAbs.

Figure 6:
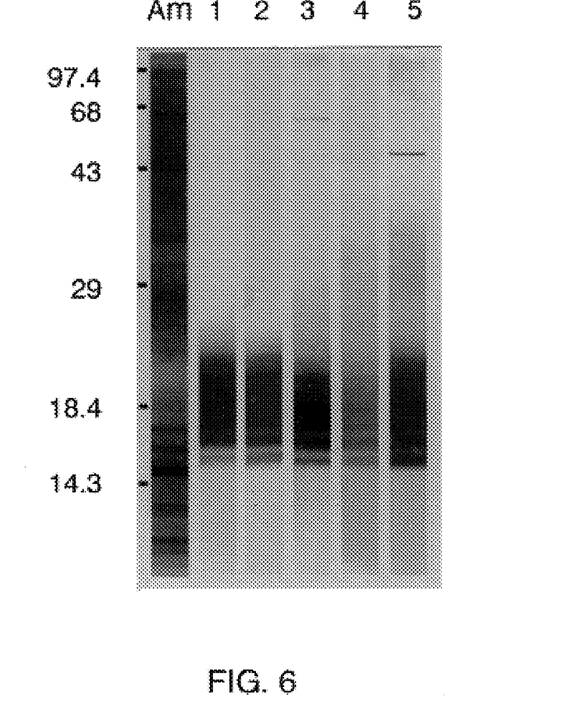
FIG. 6 is a Western immunoblot reflecting sperm extract on gel combined with a panel of sperm-binding monoclonal antibodies.

Published and preliminary results suggest that our S19 mAb and the H6-3C4 mAb, prepared by Isojima and colleagues, react with an identical glycoprotein Kameda et al., Biol. Reprod. 46:349–357 (1992). To further investigate this cross reactivity, Dr. Koji Koyama (Hyogo Medical College, Nishinomiyz, Japan) provided the H6-3C4 mAb as well as three other mAbs that competed H6-3C4 binding to sperm and react with carbohydrate epitopes: 2C6, 2B6, and 2E5 Isojima et al, Gamete Interaction for Immunocontraception, 359–376 Wiley-Liss (1990). A human sperm extract prepared in 1% SDS was electrophoresed on an SDS-PAGE curtain gel (a 15% acrylamide slab gel with a single well extending the length of the gel) and transferred to nitrocelllose. The immunoblot was cut into vertical strips and analyzed by standard Western blot procedures with the S19, H6-3C4, 2C6, 2B6, and 2E5 mAbs (FIG. 6). Each mAb identified bands of identical molecular weight. These results indicate that the S19, H6-3C4, 2C6, 2B6 and 2E5 mAbs react with the same human sperm membrane glycoprotein, SAGA-1. The H6-3C4 heterohybridoma was generated using lymphocytes from an infertile woman whose serum agglutinated human spermatozoa and contained sperm-immobilizing antibodies. Thus, SAGA-1 has been identified as one antigen recognized by human females with antisperm antibodies and infertility. (FIG. 6: A, amido black staining; Lane 1, S19; Lane 2, 2E5; Lane 3, H6-3C4; Lane 4, 2B6; Lane 5, 2C6.)

Microsequence Analysis Demonstrated that SAGA-1 is Homologous with CDw52, a GPI-anchored Glycoprotein on the Lymphocyte Cell Surface.

As noted, partitioning of hydrophobic sperm proteins was used as a first step towards the purification of SAGA-1. Sperm proteins present in the TX-114 detergent phase were precipitated under acetone and, alternately, proteins extracted in chloroform/methanol were dried to completion by rotary evaporation and lyophilization. These hydrophobic protein pellets were resuspended in 0.5% octyl glucoside (OG). To prepare an immunoaffinity matrix, S19 mAbs were chemically crosslinked to Protein-G Sepharose beads (Pharmacia) with dimethyl pimelimidate Schneider et al., J. Biol. Chem. 257:10766–10769 (1982). This immunomatrix was used to affinity purify SAGA-1 from the pool of hydrophobic sperm proteins and a yield of 200 $\mu$g of native SAGA-1 was obtained.

Figure 7:
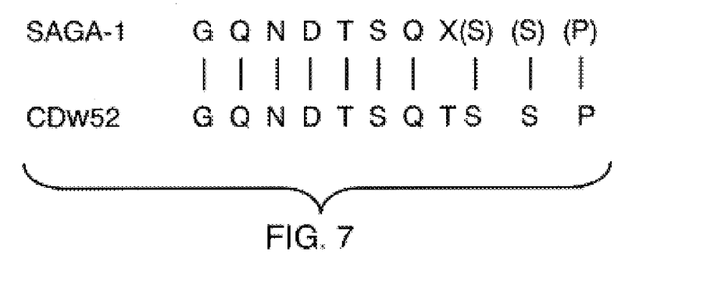
FIG. 7 reflects the homology of a microsequence of SAGA-1 (SEQ ID NO. 1) with the glycoprotein CDw52 (SEQ ID NO. 2).

Following one-dimensional SDS-PAGE, immunoaffinity purified SAGA-1 was electroblotted onto PVDF as described Herr et al., Biol. Reprod. 47:11–20 (1992) and the blot was cut in half. Immunostaining with the S19 mAb was used to identify SAGA-1 on one half of the blot. The corresponding portion of the non-immunostained half was excised and SAGA-1 was microsequenced by Edman degradation. The first seven amino acids were determined to by GQNDTSQ, (SEQ ID NO: 3) the eighth amino acid was undetermined (designated X), and the ninth, tenth, and eleventh amino acids were assigned as SSP (shown in parentheses to indicate the tentative nature of these assignments). This sequence is homologous to the first eleven amino acids of the twelve amino acid peptide core of the mature CDw52 glycoprotein. The first seven amino acids of SAGA-1 and of CDw52 show 100% identity. (FIG. 7: Microsequence of SAGA-1 (SEQ ID NO: 1) and homology with CDw52. (SEQ ID NO: 2)

The S19 mAb and an Anti-CDW52 mAb React With the Same Protein in Sperm Extracts.

Figure 8:
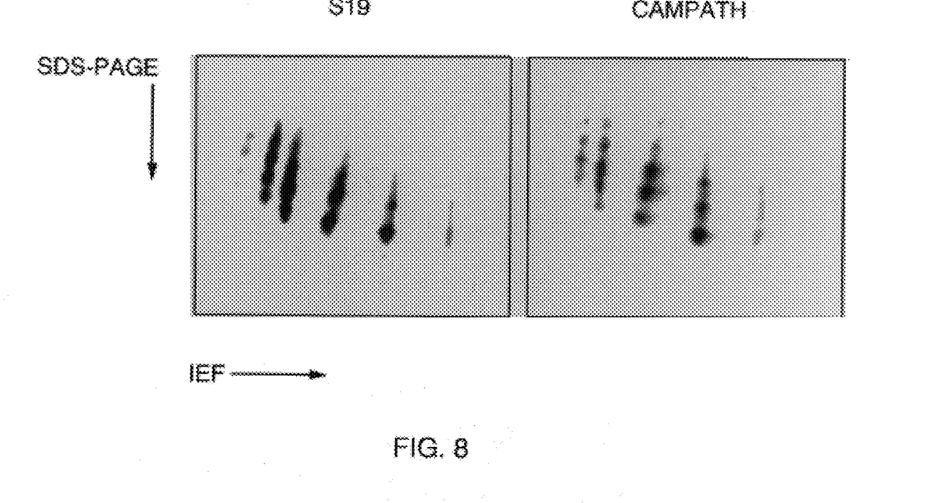

Two-dimensional immunoblots of sperm proteins were incubated with the S19 mAb and CAMPATH-1M, a mAb that reacts with an epitope spanning the C-terminal tripeptide of CDw52 and its GPI-anchor Xia et al., Biochem. J. 293:633–640 (1993). The S19 (FIG. 8A) and CAMPATH-1M (FIG. 8B) mAbs identified nearly identical patterns of immunoreactive spots (~15–25 kDa and ~pI 2.5–3.0). These results indicate that the S19 and CAMPATH-1M mAbs react with epitopes present on the same sperm glycoprotein. Furthermore, fluorescein-conjugated S19 and CAMPATH-1M mAbs exhibited the same pattern of immunofluorescence over the entire sperm membrane. (FIG. 8: Two-dimensional immunoblots of sperm proteins. A, Immunoblot with the S19 mAb; B, Immunoblot with the CAMPATH-1M mAb.)

SAGA-1 on Spermatozoa Contains Unique Carbohydrate Epitopes not Found on Lymphocytes.

Figure 9:
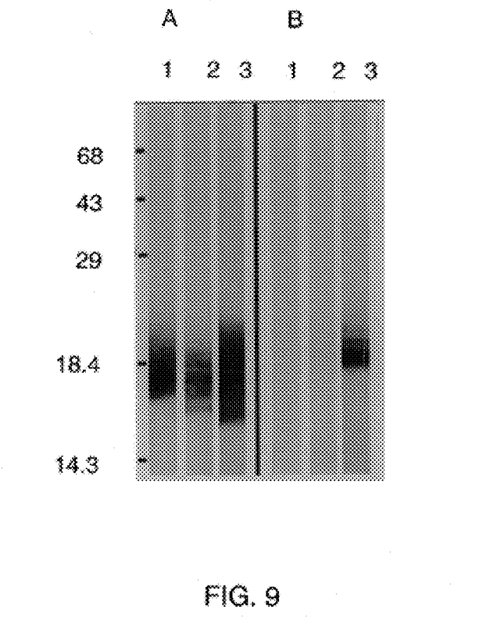
FIG. 9 compares the immunoreactivity of various sperm antibodies with proteins extracted from human sperm and spleen.

To compare the immunoreactivity of the S19, H6-3C4, and CAMPATH-1M mAbs, hydrophobic proteins extracted with chloroform/methanol from human spermatozoa and spleen were subjected to immunoblot analysis. Spleen tissue was employed as a source of lymphocyte proteins. The S19, H6-3C4, and CAMPATH-IM mAbs identified a ~15–25 kDa series of protein bands in the sperm extract (FIG. 9A). However, in the spleen extract, the CAMPATH-1M mAb detected a series of higher molecular weight bands than in the sperm extract while neither S19 nor H6-3C4 reactivity was detected (FIG. 9B). Therefore, the S19 and H6-3C4 carbohydrate epitopes are not present on CDw52 or other glycoproteins in the spleen extract. These results indicate that while the SAGA-1 and CDw52 core proteins are highly homologous, their carbohydrate structures are immunologically and structurally distinct. SAGA-1 and CDw52, therefore, are glycoforms, i.e. glycoproteins with the same core peptide but with differing carbohydrate structures. (FIG. 9: A, Sperm extract; B, Spleen extract. Lane 1, Immunoblot with the to S19 mAb; Lane 2, Immunoblot with the H6-3C4 mAb; Lane 3, Immunoblot with the CAMPATH-1M mAb.)

S19 Immunoreactivity was Demonstrated in the Human Epididymis and this Expression of the S19 Carbohydrate Epitope is Apparently Tissue-specific and not Found in the Tissues of the Human Female Reproductive Tract.

S19 immunostaining was not detected on immunoblots of post-vasectomy semen samples, while the S19 mAb reacted with the 15–25 kDa series of protein bands in a sperm extract. Therefore, the S19 epitope was not identified on a glycoprotein component of post-vasectomy seminal plasma. These results suggest that the S19 epitope and the SAGA-1 glycoprotein are products of the epididymis or proximal vas deferens, but not the testis, distal vas deferens, seminal vesicle, or prostate.

Figure 10A:
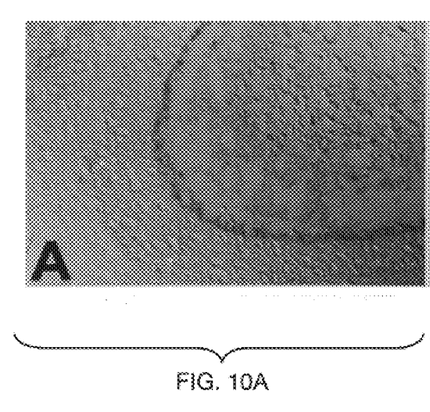
In FIG. 10A an epididymal section was incubated with the S19 antibody and a secondary antibody for detection, while 10B is a control, reflecting a section incubated with the secondary antibody, but not S19.
Figure 10B:
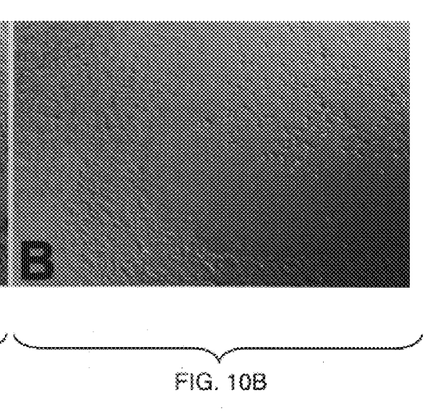

Sections of formalin-fixed, paraffin-embedded human epididymis were subjected to immunohistochemical staining with the S19 mAb. A blue precipitate formed by the horseradish peroxidase substrate True Blue (Kirkegaard and Perry Laboratories) identified S19 immunoreactivity on the stereocilia of the epithelial cells surrounding the epididymal lumen and on spermatozoa present in the lumen. Furthermore, S19 immunoreactivity was not detected in human testis sections by immunohistochemical analysis. These findings and the results of Yeung et al. Mol. Reprod. Dev. 48:267–275 (1977) with the CAMPATH-1M mAb suggest that SAGA-1/CDw52 is secreted by the epididymal epithelium and is inserted into the sperm phasmalemma during epididymal maturation. (FIG. 10: Immunohistochemical analysis of human epididymis visualized with differential interference [DIC] microscopy. A, Section incubated with the S19 mAb; B, Section incubated with secondary antibody alone.)

Additional immunohistochemical studies and immunoblot analysis of human tissue did not identify S19 immunoreactivity in the spleen, kidney, lymph node, isolated lymphocytes, nor tissues of the female reproductive tract including vagina, cervix, uterus, and fallopian tube (Table 1). These findings indicate that the S19 carbohydrate epitope is expressed specifically in the epididymis. The lack of expression of the S19 epitope in tissues of the female reproductive tract, including vagina and cervix, make application of the S19 in a spermistatic, particularly attractive.

Synthetic S19 carbohydrate epitope and peptides that mimic the conformation of the S19 carbohydrate epitope may serve as the basis for the development of a contraceptive vaccine. The S19 mAb is crucial for the identification of the cognate epididymal-, sperm-specific S19 carbohydrate epitope and for the identification of peptides that mimic the conformation of the S19 carbohydrate epitope. Synethetic S19 carbohydrate epitope and peptide mimics may serve as immunogens for development of a contraceptive vaccine.

UTILITIES

1) The development of a contraceptive vaccine. Purified SAGA-1 is crucial for the procurement of reagents and information necessary to identify SAGA-1-specific carbohydrate epitopes. Synthetic SAGA-1 carbohydrate epitopes and peptide mimics of SAGA-1 carbohydrate epitopes may serve as contraceptive immunogens. SAGA-1 immunization will generate antibodies in the host, sufficient for the purposes of inhibition of fertilization. The demonstration herein of the unique carbohydrate character of the immunogen epitope, and its epididymal/sperm specific nature enhance its value as the active agent of a vaccine. The complete absence of this immunogen from the female reproductive system further enhances its effectiveness. The distribution of this immunogen over the entire surface of the sperm further ensures the effectiveness of a vaccine based thereon, since actively generated antibodies thereto have full access to the epitope over all of the surface domains of the spermatozoa. Preparation of the vaccine itself follows a traditional format. The purified immunogen, preferably a recombinant immunogen having the S19 epitopic regions, a synthetic carbohydrate S19-recognized epitope bearing immunogen or a peptide mimic of the S19 epitope is incorporated in a suitable pharmaceutical carrier.

The preparation of an acceptable vaccine, using Applicants novel immunogen, can be obtained following traditional methods. The vaccines described using earlier developed immunogens, discussed above, can be easily adapted to the SAGA-1 protein, and its derivatives bound by the S19 mAb. In particular, contraceptive vaccines employing the PH-20 protein developed by Primakoff, supra and Primakoff, Am. J. Reprod. Immunol., 31:208–210 (1994) reflect a successful adaptation of a sperm protein antigen to a vaccine immunogen in a suitable carrier. While the proteins employed in Primakoff and the others were unfortunately unable to give a high (in excess of 80% or better, preferably 90% or better, most preferably at least 95%) degree of fertilization inhibition in primates, the specific characteristics of the SAGA-1 protein, in particular, its thorough distribution over the entire surface of the sperm cell and its carbohydrate epitope localization in the extracelluar glycocalyx, impart increased surface area and accessibility for antibody binding, and thus, provide an opportunity to achieve fertilization inhibition on the order of oral contraceptives (i.e., 99 percent).

To develop adequate antibody titer, it is probable that most test subjects, including female humans, will need to be vaccinated according to a protocol with widely spaced injections, to give time for the generation of the appropriate antibody titer after each injection. Injections administered about one month apart, followed by an assay using the SAGA-1 protein as a standard for determining antibody titer, should be adequate after a period of about three months to give sufficient fertilization inhibition for purposes of reliable use. Of course, where the diagnostic assay reflects a lower antibody titer, such that nearly complete fertilization inhibition is not provided, a further vaccination program, or other testing to determine the reason for low antibody titer, should be undertaken.

The use of an immunogen to generate antibodies to the natural state antigen, or a recombinant antigen, both of which are embraced by the claimed invention, is, per se, routine to those of ordinary skill in the art. The inventors' novel development extends to the incorporation and reliance on the unique SAGA-1 protein, first fully characterized herein. Routine optimization of dosages, vehicles, presentation modes and the like do not constitute an aspect of the invention, per se. Nonetheless, it is suggested, as a routine dosage that a dosage range of 100 $\mu$g SAGA-1 protein –500 $\mu$g SAGA-1 protein in a volume of 0.5 ml, be suitable as an individual dosage value. Because the antibodies generated by the vaccination program will agglutinate sperm more effectively than other specific anti-sperm antibodies, due to binding over an increase surface area and localization of the carbohydrate in the extracellular glycocalyx, enhanced effectiveness of the vaccine is obtained.

As is common with most vaccines, a multivalent vaccine is frequently more effective than a single one. As noted previously, numerous sperm-specific antigens, in addition to SAGA-1, are known. Although, individually, these antigens do not give rise to a high degree of confidence of fertilization inhibition in primates, they can be added to a SAGA-1-based vaccine to give further reliability. In particular, a combination of SAGA-1 and SP-10 is desirable as the immunogen mixture for a multivalent vaccine. Since research demonstrates that antibodies to these proteins are readily developed, the generation of combined binding ability to both proteins, as well as other art-recognized proteins that may be added as immunogenic members of a multivalent vaccine, is possible. It is essential, however, that the SAGA-1 protein, or any variant protein bound by the S19 antibody, be a central element of the vaccine, as the antibodies thereto provide greatly enhanced binding opportunities, and therefore, a greater degree of confidence of fertilization inhibition.

2) The development of a diagnostic test for clinical evaluation of an individual's response to a SAGA-1 contraceptive vaccine. Such a test will measure the titer of anti-SAGA-1 antibodies and can be developed as a clinical diagnostic kit for monitoring fertility status in individuals receiving a SAGA-1 contraceptive vaccine. Additionally, qualitative testing for the presence of SAGA-1, and therefore sperm, may find important application.

The properties of the immunogen bound by the S19 mAb, including the SAGA-1 protein, make two different types of diagnostic testing possible. Initially, it is necessary to monitor the development of antibodies to the vaccine immunogen, the SAGA-1 protein or variants thereof. Certain potential candidates may lack a suitable immune response system, and many individuals vary in the antibody titer generated in response to any immunogen or protocol of immunogen administration. Development of an adequate antibody titer may be easily confirmed using the SAGA-1 protein as an antigen standard. Using the agglutination assay described above with respect to the S19 mAb, one can easily determine the concentration necessary for 100 percent agglutination. This concentration of SAGA-1 protein, properly immobilized and presented, is tested against a sample drawn from the patient. Achievement of 100 percent binding suggests an adequate antibody titer. Because any such vaccination program must be conducted under clinical supervision, the testing format may be conventional, using ELISA, Western blotting analysis or other established art formats.

There is in addition, increasing interest in simple-to-use, "user friendly" commercial diagnostics, that is, over the counter diagnostics. The reasons for interest in this type of diagnostic, and the variety of uses for such a diagnostic, are discussed in detail in U.S. Pat. No. 5,605,803 which is incorporated herein by reference. The diagnostics disclosed therein employ the SP-10 binding antibody, MHS-10, or antibodies having the binding characteristics of those expressed by a hybridoma cell line at the ATCC available under Accession No. HB 10039. As described in the incorporated patent, this type of over the counter diagnostic finds application in forensic environments, can be useful in determining the presence of normal germ cell lineage, finds substantial value in those experiencing difficulty in achieving conception, in vasectomized males and the testing of vasectomized males, both by males and females, as well as the testing of vasovasostomized males, to determine the success of surgical reconnection. For any of a variety of reasons, determination of the presence of sperm in a biological sample, either an ejaculate or a sample derived from an ejaculate or from the male reproductive tract, is of significant medical importance. The antigen bound by the S19 mAb, the SAGA-1 protein and corresponding variants, mimics and recombinant derivatives, having the S19 responsive carbohydrate epitope, can be employed in assay formats such as those described in the incorporated U.S. Pat. No. 5,603,803.

Thus, the S19 antibody may be bound to a solid phase and used to capture the SAGA-1 protein. Recognition of the presence of the SAGA-1 antigen may be completed by use of a second monoclonal or polyclonal reagent. See, e.g., Shen et al., Am. J. Reprod. Immunol., 29:231–240 (1993). Other assay formats could utilize a wick or dipstick, and antibody coded colored beads. In all these variations, the essential reagent is the S19 mAb, or similar antibody to the SAGA-1 protein. Any protein present in the sample tested is bound or captured by the immobilized antibody. Thus, in the diagnostic intended to monitor development of adequate antibody titer, the SAGA-1 protein or similar protein is used as the standard test reagent. In the "home test kit", wherein verification of the presence of the immunogen is desired, thereby verifying the presence of sperm, the monoclonal antibody responsive thereto is the reagent.

3) The development of agglutinins for a topical spermistatic. Monoclonal and polyclonal antibodies produced against SAGA-1 will be used as agglutinins for the further development of a topical spermistatic.

As noted, the literature theorizes the development of a variety of monoclonal antibody-based spermicides. Suitable vehicles are described in Cone and Alexander, supra. Applicants have developed a particular vehicle for the presentation of mAb S19 in agglutinating form, by using the commercially available liposome delivery system available from Novavax, Inc. of Rockville, Md., commercially available under the name Novasomes®. These liposomes are specifically formulated for antigen or antibody delivery. Novasomes® containing native S19 monoclonal antibody molecules bound to the surface of these non-phospholipid positively charged liposomes function effectively as a spermistatic in a spermicide type gel. The Novasome® formulation was tested using the sperm agglutination assay described. At a 1:10 dilution the S19-Novasome® vehicle agglutinated sperm at the same efficiency as a 1:20 dilution of the S19 ascites fluid. These results indicate that the S19 monoclonal antibody has the same effect on sperm function when incorporated into commercially available delivery systems, as in native fluid.

Alternative delivery systems are available to those of skill in the art. Prominent among these are lipid-conjugated peptides, see, e.g., Deres et al., Nature, 342:561–564 (1989) and ISCOMs, see, e.g., Takahashi, Nature, 344:873–875 (1990). Other preparations, including hydrophobic emulsions and saponins, have been developed in the past for the processing and presentation of specific peptides, and may be used in connection with the antibodies of the spermicide addressed here. See, e.g., Raychaudhuri et al., Proceedings of the National Academy of Science, U.S.A., 89:8308–8312 (1992) and Newman et al., J. Immunol., 148:2357–2362 (1992). Other vehicles, including the presentation of the antibodies on a membrane, such as that expressed by recombinant virus (i.e., recombinant viral schemes wherein the DNA encoding the antibody, see, infra, is expressed in an recombinant cell together with a structural membrane protein) may be used. Of the available varieties, in addition to the non-phospholipid liposomes described above, immune-stimulating complexes or ISCOMs, commonly used in vaccines for the presentation of antigens, offer desirable features. ISCOMs form cage-like membrane structures into which or on which the antibody can be presented. ISCOMs have previously been used in connection with the presentation of antigens, but they similarly present antibody proteins in an exposed, virus-like structure. In this respect, other vehicles known for the presentation of active proteins, including co-polymer spheres, and virus-like particles (VLPs) have been known to achieve results similar to the ISCOMs. Of course, a system conventional in the extreme, the attachment of the antibody, via coupling agent, to the surface of a microsphere, may be suitably used in conjunction with acceptable manufacturing techniques for the formulation of gels and creams consistent with this approach.

Thus, the essence of Applicants spermistatic is the incorporation, in a suitable carrier, of a sufficient concentration of S19 mAb in an appropriate vehicle to effectively inhibit (agglutinate or bind) all sperm present in an ejaculate, or otherwise effectively preclude cervical penetration by sperm.

The invention has been described generically, and by reference to specific embodiments. Alternatives to the specific embodiments will occur to those of ordinary skill in the art without the exercise of inventive faculty, and such embodiments are not intended as limiting the invention, save where recited in the claims. In particular, alternatives to presentation format, dosages, vehicles, regimens, constructs and peptides are enabled by the disclosure above, but do not fall outside the intended scope of the invention, unless excluded by the recitations of the claims set forth below.

TABLE 1

Immunohistochemical studies with the S19 monoclonal antibody. Identification of S19 Immunoreactivity Exclusively in Spermatozoa and the Epididymis.*

| TISSUE/CELL TYPE | IMMUNOHISTOCHEMISTRY | IMMUNOBLOT ANALYSIS |
| --- | --- | --- |
| Spermatozoa | + | + |
| Epididymis | + | NA |
| Testis | – | NA |
| Kidney | NA | – |
| Lymph Node | NA | – |
| Spleen | – | – |
| Isolated Lymphocytes | NA | – |
| Vagina | – | NA |
| Cervix | – | NA |
| Uterus | – | NA |
| Fallopian Tube | – | NA |

NA: Not Applicable
*The absence of immunoreactivity of the S19 mAb with female reproductive tissues reenforces the application of the S19 mAb as a spermicide.

What is claimed is:

1. An isolated carbohydrate epitope that binds to a monoclonal antibody expressed by Hybridoma cell line HB-12144.

2. A composition, said composition comprising the carbohydrate epitope of claim 1 in a pharmaceutically acceptable carrier.

* * * * *